United States Patent
Overton

(10) Patent No.: US 9,399,202 B2
(45) Date of Patent: Jul. 26, 2016

(54) APPARATUS, SYSTEM AND METHOD FOR MIXING AND DISPENSING DENTAL IMPRESSION MATERIALS

(71) Applicant: Bradford D. Overton, Broken Arrow, OK (US)

(72) Inventor: Bradford D. Overton, Broken Arrow, OK (US)

( * ) Notice: Subject to any disclaimer, the term of this patent is extended or adjusted under 35 U.S.C. 154(b) by 0 days.

(21) Appl. No.: 14/733,362

(22) Filed: Jun. 8, 2015

(65) Prior Publication Data
US 2015/0265981 A1 Sep. 24, 2015

Related U.S. Application Data

(60) Division of application No. 14/639,839, filed on Mar. 5, 2015, now Pat. No. 9,089,381, which is a continuation of application No. 14/522,149, filed on Oct. 23, 2014, now Pat. No. 9,010,993, which is a continuation-in-part of application No. 12/823,152, filed on Jun. 25, 2010, now abandoned.

(51) Int. Cl.

| | |
|---|---|
| *B01F 7/16* | (2006.01) |
| *B01F 9/00* | (2006.01) |
| *B01F 13/00* | (2006.01) |
| *B01F 7/00* | (2006.01) |
| *B01F 15/00* | (2006.01) |
| *A61K 6/10* | (2006.01) |
| *B01F 7/30* | (2006.01) |

(Continued)

(52) U.S. Cl.
CPC .......... *B01F 7/00583* (2013.01); *A61C 1/0061* (2013.01); *A61C 9/0026* (2013.01); *A61K 6/10* (2013.01); *B01F 3/1228* (2013.01); *B01F 7/007* (2013.01); *B01F 7/00058* (2013.01); *B01F 7/00725* (2013.01); *B01F 7/161* (2013.01); *B01F 7/165* (2013.01); *B01F 7/1655* (2013.01); *B01F 7/1695* (2013.01); *B01F 7/30* (2013.01); *B01F 7/32* (2013.01); *B01F 9/00* (2013.01); *B01F 13/002* (2013.01); *B01F 13/06* (2013.01); *B01F 15/0085* (2013.01); *B01F 15/00487* (2013.01); *B01F 15/00941* (2013.01); *B01F 15/029* (2013.01); *B01F 15/0216* (2013.01); *B01F 15/0261* (2013.01); *B01F 15/0441* (2013.01); *A47J 31/402* (2013.01); *B01F 2003/0896* (2013.01); *B01F 2215/0027* (2013.01)

(58) Field of Classification Search
None
See application file for complete search history.

(56) References Cited

U.S. PATENT DOCUMENTS

| | | | | |
|---|---|---|---|---|
| 5,938,325 A | * | 8/1999 | Edwards | B01F 7/00066 366/129 |
| 7,469,801 B2 | * | 12/2008 | Ramirez-Delgado | A61C 9/0026 222/129 |
| 8,414,180 B1 | * | 4/2013 | Mattingly | B01F 7/00283 366/247 |

*Primary Examiner* — Neil N Turk
(74) *Attorney, Agent, or Firm* — Frederic Dorwart, Lawyers; Penina Michlin Chiu

(57) ABSTRACT

An apparatus, system and method for mixing and dispensing dental impression materials is described. A dental impression material mixing machine comprises a water dispenser fluidly coupled to a hollow mixing axle, the mixing axle extending through a pulley, wherein an inner circumference of the hollow mixing axle forms a water conduit and an outer circumference of the hollow mixing axle forms a hub connector, a closeable valve inserted at a water entrance to the water conduit and electronically coupled to a water pump, an electronically commutated motor rotateably coupled to the pulley, wherein the hub connector receives a tubular rotatable hub of a disposable mixing vessel comprising dry dental impression powder, and wherein water is dispensed from the water dispenser into the disposable mixing vessel through the water conduit and hub orifice.

3 Claims, 7 Drawing Sheets

(51) Int. Cl.
*A61C 1/00* (2006.01)
*A61C 9/00* (2006.01)
*B01F 7/32* (2006.01)
*B01F 13/06* (2006.01)
*B01F 15/02* (2006.01)
*B01F 15/04* (2006.01)
*B01F 3/12* (2006.01)
*A47J 31/40* (2006.01)
*B01F 3/08* (2006.01)

APPARATUS, SYSTEM AND METHOD FOR MIXING AND DISPENSING DENTAL IMPRESSION MATERIALS

CROSS REFERENCE TO RELATED APPLICATIONS

The present application is a divisional of U.S. application Ser. No. 14/639,839 to Overton filed Mar. 5, 2015 and entitled "APPARATUS, SYSTEM AND METHOD FOR MIXING AND DISPENSING DENTAL IMPRESSION MATERIALS", which is a continuation of U.S. application Ser. No. 14/522,149 to Overton filed Oct. 23, 2014 and entitled "APPARATUS, SYSTEM AND METHOD FOR MIXING AND DISPENSING DENTAL IMPRESSION MATERIALS," now U.S. Pat. No. 9,010,993, which is a continuation-in-part of U.S. application Ser. No. 12/823,152 to Overton et al. filed Jun. 25, 2010 and entitled "METHOD AND APPARATUS FOR PREPARING AND DISPENSING DENTAL ALGINATE COMPOUND", each of which are hereby incorporated by reference in their entireties.

BACKGROUND OF THE INVENTION

1. Field of the Invention

Embodiments of the invention described herein pertain to the field of viscous, thixotropic impression materials. More particularly, but not by way of limitation, one or more embodiments of the invention enable an apparatus, system and method for mixing and dispensing dental impression materials.

2. Description of the Related Art

During the practice of dentistry or orthodontics, it becomes necessary from time to time to take an impression of a patient's teeth in order to provide treatment or to complete a required procedure, such as filling a cavity or fitting a retainer. Conventionally, creating an oral impression is a two step process, which occurs in a dentist or orthodontist's office. First, an impression or negative mold of the patient's teeth is created. To create the mold, a viscous, thixotropic impression material, typically sodium alginate, is prepared by measuring a powder (e.g., alginate powder), and then mixing the powder with a precise quantity of water in an open container or bowl using a paddle or spatula. The impression material is mixed until smooth and even in consistency, forming a paste, after which it is put into a dental impression tray and placed in the patient's mouth. After a short period of time, the impression compound sets and becomes firm. Upon removal from the patient's mouth, an impression of the patient's dental arrangement is left in the tray.

The next step is to create a cast from the mold. A plaster derivative, such as dental stone, is prepared, again by measuring out and mixing a dry powder with a precise quantity of water to form a paste. The paste is mixed with a spatula in a bowl, and is then scooped into the dental impression mold to cast a mock-up of the patient's dental arrangement (teeth) once the paste dries. From this model, the dentist or orthodontist may plan treatment procedures, or make dental appliances suitable for the specific patient's dental arrangement.

Currently, the measuring and mixing required to prepare the impression materials is a tedious, messy and cumbersome manual process. Quantities of dry powder and water must be carefully measured, the wetted powders must be thoroughly and evenly mixed by hand, and once mixed, scooped and transferred into the impression tray. In a typical alginate impression, 1-2 ounces of water and about 2 ounces of powder must be carefully combined and then spatulated aggressively to reach a creamy consistency. The whole process must be completed quickly and with considerable force. For example, if the process is not completed quickly enough, the compound may prematurely set. If enough force is not used, the mixture may not reach the necessary smooth and creamy consistency.

There are a number of difficulties with this common method of dental impression preparation. One problem is the consistency and uniformity required of the impression compound mixtures. The ratio of water to powder is required to be precise, and this precision is dependent on the complete incorporation of water into the powder. If some of the powder is un-wetted and unmixed due to being in inaccessible places in the mixing cup or poor mixing technique, the ratio of water to powder is effectively too high, and the compound will not perform properly. Areas of unmixed powder may also clump and not flow properly.

The impression compound is also sensitive to the formation and entrapment of bubbles, which bubbles negatively affect the smoothness of the resulting molds and casts. In addition, the impression powder is prone to "slumping". This causes a disparity between the required amount and the actual dispensed amount, which discrepancy can be as high as 30%.

Another problem is that the impression and dental stone compounds consist of a fine powder before being mixed with water. This powder becomes air-borne during the preparation process, and can be irritating if inhaled. Additionally, the powder can get into instruments and equipment in the dental office, some of which are quite expensive and intolerant to this type of contamination.

A further problem is the sterility and cleanliness of the equipment used to mix the compounds. Every item going into the patient's mouth during dental and orthodontic procedures must be sterilized, usually by use of an autoclave, a type of oven that applies heat, which kills any harmful micro-organisms that may reside on the instruments or appliances being sterilized. The paddles, bowls and other equipment currently used to prepare impression compound are not able to withstand the heat of the autoclave procedure, and are therefore difficult to sterilize.

Yet another problem arises once the impression material or plaster derivative is mixed and must be transferred to the impression tray. It is difficult to efficiently transfer the compound without leaving much of it behind in the mixing cup. Once the impression process is complete, a sticky mess is left behind with many bowls, spatulas and/or spoons to disinfect.

Currently, polyvinyl siloxane is sometimes used as a mold material, rather than sodium alginate, in an attempt to address some of the problems associated with the preparation of dental impression materials. Polyvinyl siloxane is an elastomeric epoxy that results from combining two viscous liquids, rather than mixing dry powder with water. These viscous liquids are sometimes dispensed with a squeeze gun. However, polyvinyl siloxane is between ten and twenty times the cost of sodium alginate, and is therefore often cost prohibitive. In addition, even if polyvinyl siloxane is used as the impression compound, the dental stone for the cast must still be mixed with water from a dry powder in the aforementioned manner.

Thus, mixing and dispensing dental impression materials using conventional systems and methods suffers from a large number of shortcomings. Therefore, there is a need for an apparatus, system and method for mixing and dispensing dental impression materials.

BRIEF SUMMARY OF THE INVENTION

An apparatus, system and method for mixing and dispensing dental impression materials is described. An illustrative embodiment of a dental impression material mixing vessel comprises a disposable vacuum-formed receptacle comprising a flexible tubular wall having a groove circumferentially about a top side of the flexible tubular wall, and a rounded bowl contiguous with the flexible tubular wall and forming a bottom of the disposable vacuum-formed receptacle, the rounded bowl having a slit at a base and comprising a removable adhesive sealedly enclosing the slit, a rigid rim inset in the groove, and a mixing assembly comprising a lid sealedly inserted into the rigid rim, wherein a portion of the flexible tubular wall is foldedly sandwiched between an inner diameter of the rigid rim and an outer diameter of the sealedly inserted lid, and wherein the lid comprises a central round opening, a tubular rotatable hub fit into the central round opening and extending partially inside and partially outside the disposable vacuum-formed receptacle, wherein a portion of the rotatable tubular hub extending inside the disposable vacuum-formed receptacle has a series of apertures spaced circumferentially and evenly about the tubular hub, and a flexible cord threaded through opposing apertures to form at least two loops of the flexible cord, the at least two loops extending from the tubular hub contouredly along an inner surface of the flexible tubular wall and rounded bowl, wherein the at least two loops cross each other at the base. In some embodiments, the disposable vacuum-formed receptacle further comprises a pre-measured amount of dry dental impression powder. In certain embodiments, the dry dental impression powder is one of alginate powder or dental stone powder. In some embodiments, there are two loops of flexible cord set at ninety degrees from one another. In certain embodiments, the at least two loops sweep about the inner surface of the flexible tubular wall and rounded bowl as the tubular rotatable hub rotates, the loop rotation mixes a dry dental impression powder inside the disposable vacuum-formed receptacle with water that enters the disposable vacuum-formed receptacle through the tubular rotatable hub to form dental impression paste and the disposable vacuum-formed receptacle is collapsible and the dental impression paste is dispensed through the slit to a dental tray as the receptacle is collapsed.

An illustrative embodiment of a dental impression material mixing machine comprises a water dispenser fluidly coupled to a hollow mixing axle, the hollow mixing axle extending centrally through a pulley, the water dispenser comprising a water pump inside the water dispenser, the mixing axle rotatable by the pulley in both a clockwise and counterclockwise direction, wherein an inner circumference of the hollow mixing axle forms a water conduit, and wherein an outer circumference of the hollow mixing axle forms a hub connector, a platform at least partially surrounding the hollow mixing axle, the platform comprising a protuberance that mates to a depression on a lid of a disposable mixing vessel, a closeable valve inserted at a water entrance to the water conduit and electronically coupled to the water pump, and an electronically commutated motor rotateably coupled to the pulley, wherein the hub connector receives a tubular rotatable hub of the disposable mixing vessel, the disposable mixing vessel comprising dry dental impression powder, the tubular rotatable hub extending through a central opening of the lid, and wherein water is dispensed from the water dispenser into the disposable mixing vessel through the water conduit and the tubular rotatable hub. In some embodiments, the closeable valve is one of a solenoid-operated valve or a vacuum-actuated valve.

An illustrative embodiment of a method for mixing and dispensing dental impression material comprises attaching a disposable mixing vessel to a mixing machine, the disposable mixing vessel comprising a pre-measured amount of dry alginate powder, entering into the mixing machine a quantity of water to be mixed with the dry alginate powder by the mixing machine, activating the mixing machine to dispense the quantity of water into the disposable mixing vessel and mix the quantity of water with the dry alginate powder to form a paste, removing an adhesive from a slit in the disposable mixing vessel, compressing the disposable mixing vessel to dispense the paste from the slit in the disposable mixing vessel, and discarding the disposable mixing vessel. In some embodiments, the method further comprises attaching a second disposable mixing vessel to the mixing machine, the second disposable mixing vessel comprising a pre-measured amount of dry dental stone powder, entering into the mixing machine a second quantity of water to be mixed with the dry dental stone powder by the mixing machine, activating the mixing machine to dispense the second quantity of water into the second disposable mixing vessel and mix the second quantity of water with the dry dental stone powder to form a second paste, removing an adhesive from a second slit in the second disposable mixing vessel, compressing the second disposable mixing vessel to dispense the second paste from the second slit in the second disposable mixing vessel, and discarding the second disposable mixing vessel.

In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

The above and other aspects, features and advantages of the invention will be more apparent from the following more particular description thereof, presented in conjunction with the following drawings wherein.

Figure 1A:
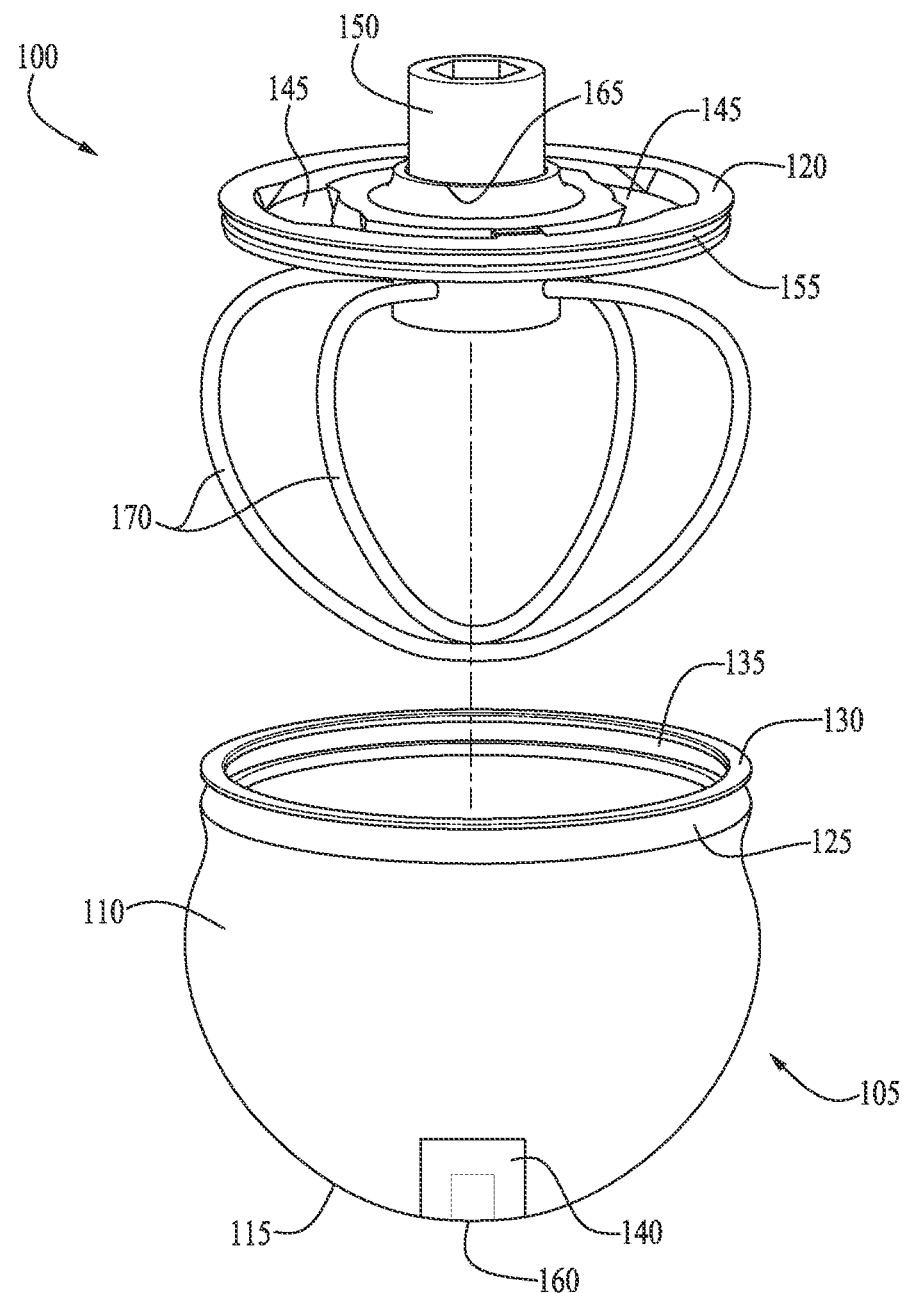
FIG. 1A is a perspective view of a mixing vessel of an illustrative embodiment with the lid open.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

An apparatus, system and method for mixing and dispensing dental impression materials will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

As used in this specification and the appended claims, the singular forms "a", "an" and "the" include plural referents unless the context clearly dictates otherwise. Thus, for example, reference to a flexible cord may also refer to multiple flexible cords.

As used in this specification and the appended claims, the term "dental impression material" refers to thixotropic impression materials such as sodium alginate, as well as to plaster derivatives such as dental stone, used in creating casts and/or molds for dental arrangements.

One or more embodiments provide a system for mixing and dispensing thixotropic materials. While so as not to obscure the invention, the invention is described herein in terms of a dental and/or orthodontic embodiment, nothing herein is intended to limit the invention to that embodiment. Any thixotropic or similar material that must be measured as a dry powder and expediently mixed with precise quantities of water or another liquid to produce a smooth paste, for example medical epoxies, fillers used in surgery and/or dehydrated foods, may benefit from the apparatus, system and method of illustrative embodiments. In addition, alginate impressions may be used for purposes other than dental purposes, such as arts and crafts.

Illustrative embodiments provide a consistent, clean and sterile system for preparing dental impressions and casts. Illustrative embodiments may ensure complete mixing of dry dental impression materials with water, minimizing bubbles and resulting in a paste of a predictable smooth and creamy consistency. Dry powder need not be measured by the operator, nor is it exposed to other equipment in the dental or orthodontic office. Using illustrative embodiments, no mixing containers or utensils require cleaning or sterilization. The mixing vessel may be disposable, and low cost such that it may be discarded without financial concern. For example, in some embodiments a disposable mixing vessel may be about twice the cost of dry alginate powder, which is currently about $0.60, the use of the disposable mixing vessel removing the cost of clean-up and disinfection, currently estimated at about $1.00-$2.00.

In an illustrative embodiment a disposable, flexible vessel including a resilient whisk may be pre-filled with a measured amount of dry powder to be used in creating a dental impression or cast. The vessel may attach to a water-dispensing axle on a discrete mixing machine, which may be small and light enough to sit on a counter in a dental office and/or be portable. The operator may select a quantity of water to be dispensed and mixed with the dry powder by the mixing machine. The quantity of water may, for example, be selected based upon the type of powder used and/or the preferred thickness of the resulting paste. The water-dispensing axle operates to rotate a hub of the mixing vessel whisk that conforms to the shape of the vessel, and uniformly mixes the dry powder with the water until the dental impression material has reached its desired consistency. Once the paste is ready, the disposable vessel may be removed from the machine, and the paste dispensed from the vessel by applying pressure, for example by folding, compressing and/or squeezing the vessel. Adhesive over a slit in the vessel may be removed by the operator to allow the paste to exit the vessel and be placed in a dental tray or mold. The empty vessel may then be discarded, leaving little waste, and only the dental tray to be cleaned and sterilized, or alternatively also discarded, improving the speed and ease of clean up.

Disposable Vessels

Figure 1B:
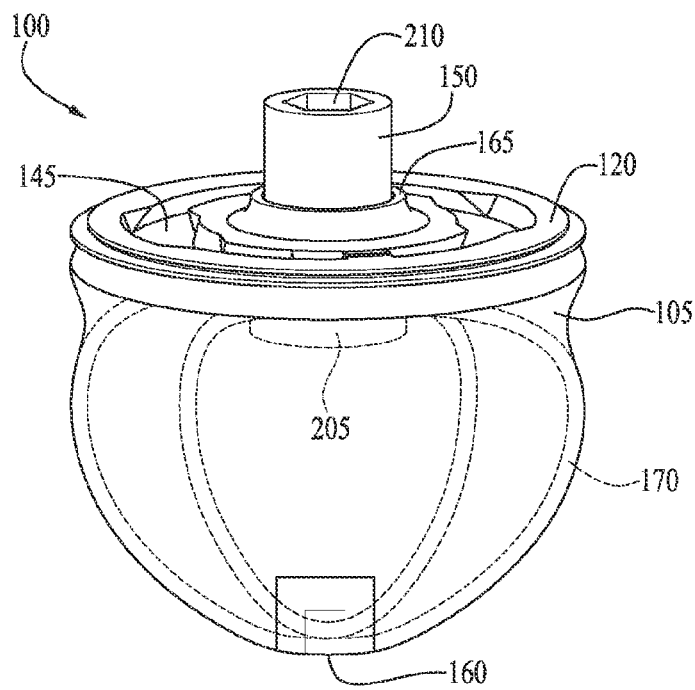
FIG. 1B is a perspective view of a mixing vessel of an illustrative embodiment with the lid closed.

A flexible, disposable mixing vessel may be employed in the system and method of illustrative embodiments. The mixing vessel may include a specific, pre-measured amount of dry dental impression material, for example 1.5 ounces, 2.0 ounces or 2.5 ounces of dry powder. The measured, dry powder may be sealed and/or contained in the vessel upon receipt by the operator, and need not be measured or poured by the operator. FIG. 1A and FIG. 1B illustrate an exemplary mixing vessel. As shown in FIGS. 1A and 1B, mixing vessel 100 includes a receptacle 105. Receptacle 105 maybe spherical and/or cylindrical in shape. In some embodiments, wall 110 may be cylindrical and/or tubular in shape and bowl 115 may be contiguous with wall 110 and rounded and/or spherical in shape. Receptacle 105 may be hollow to accommodate dry powder, water and mixing equipment, and open at a top side to accommodate lid 120. Receptacle 105 may be comprised of a thermoplastic and/or vacuum-forming material such as ethylene-vinyl acetate copolymer, also known as "soft EVA", low density polyethylene (LDPE) or other material having similar properties. Receptacle 100 may be 1 mm, 1.5 mm 2 mm, 3 mm thick or another similar thickness and be flexible and/or collapsible. In some embodiments, receptacle 105 may be transparent such that the dry powder and mixing equipment is visible to an operator during the mixing process. In certain embodiments, receptacle 105 may be trimmed and formed from a 5 inch by 5 inch square of 1 mm thick soft EVA.

Upper side of wall 110 may include groove 125 extending circumferentially about the rim of wall 110 just below the top edge. Retainer ring 130 may be inserted into groove 125 and assist in supporting receptacle 100. Retainer ring 130 may include a circumferential indentation 135 on its inner diameter such that indentation 135 may receive lid 120.

Receptacle 100 may be closed with lid 120. FIG. 1A illustrates an exemplary embodiment of lid 120 open, and FIG. 1B illustrates an exemplary embodiment of lid 120 closed. Lid 120 may be a flat, round disk that may snap, thread, twist, press and/or fit tightly into retainer ring 130 and/or indentation 135. Lid 120 may snap into indentation 135 on the inside of retainer ring 130. Receptacle 105 material may fold and/or sandwich in between the outer diameter of lid 120 and the inner diameter of retainer ring 120 such that it is pinched by the snapping of lid 120 into retainer ring 130. Pinching a portion of receptacle 105 between lid 120 and retainer ring 130 may serve to keep receptacle 105 from slipping off of retainer ring 130 and/or to provide an extra sealing mechanism. The connection between retainer ring 130 and lid 120 may be a firm connection that requires considerable pressure to press the receptacle 100 material between retainer ring 130 and lid 120 in order to form a tight seal. Receptacle 100 may include slit 160 for discharge of mixed paste. Slit 160 may be a hole, slit or other aperture that is covered with adhesive 140. Slit 160 may be at the bottom (base) of bowl 115 or at another location of bowl 115 or wall 110. Placing slit 160 at the bottom, center of bowl 115 may provide for more efficient dispensation of mixed paste. Adhesive 140 may be removable and keep receptacle 105 sealed closed until the mixed paste is ready to be dispensed.

Figure 4:
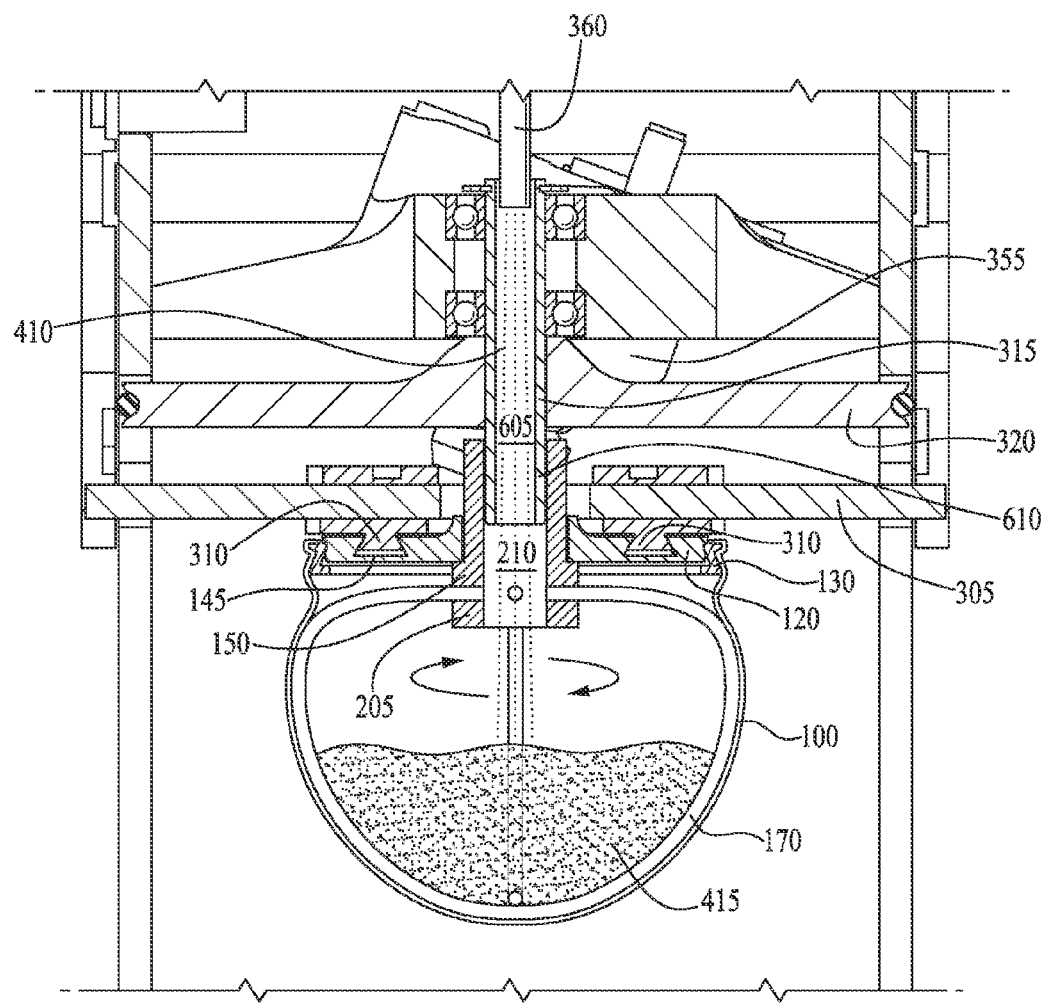
FIG. 4 is a cross sectional view across line 4-4 of FIG. 3 of a mixing machine of an illustrative embodiment.

Lid 120 may be a flat, round disk and include one or more depressions 145 on its outer surface for securing, attaching and/or fastening mixing vessel 100 onto a mixing machine. When lid 120 is closed onto receptacle 105, lid 120 may removeably lock into a protuberance on a mixing machine as shown in FIG. 4, such that mixing vessel may be attached or removed from the mixing machine as necessary. Lid 120 may include a central opening 165 for receipt of hub 150. The outer circumference of lid 120 may include recess 155 for threading, snapping and/or mating with indentation 135 on retainer ring 130. When inserted into central opening 165, hub 150 may partially extend inside receptacle 105, inside of lid 120, and partially outside of receptacle 105, outside of lid 120.

Figure 2:
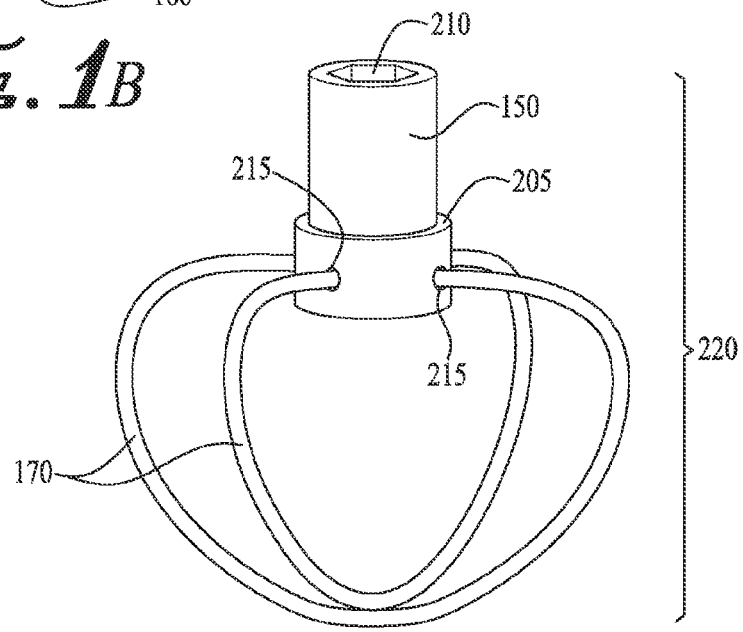
FIG. 2 is a perspective view of a whisk of an illustrative embodiment.

Hub 150 may be flanged at flange 205 so as to press up against the inner side of lid 120 when positioned within closed lid 120. Hub 150 may also include orifice 210 that may function as a water delivery port for the delivery of water into receptacle 105 and/or may mate with an axle of a mixing machine. Flange 205 and/or hub 150 may include apertures 215 evenly and circumferentially spaced about the side of hub 150 inside of receptacle 105. As shown in FIG. 2, apertures 215 may allow for cords 170 to be threaded onto hub 150 to form whisk 220. In some embodiments, four apertures 215 may be evenly spaced about flange 205 to accommodate two cords 170. Each cord 170 may form a loop inside receptacle 105, with each loop making use of two opposing apertures 215. Cords may be sized such that they contour along wall 110 and bowl 115. Cords 170 may cross at the base of bowl 115 and be arranged perpendicularly such that cords 170 are set ninety degrees from one another, as illustrated in FIG. 2. In other embodiments, three cords 170 may be spaced sixty degrees from one another. In some embodiments only one cord 170, or more than three cords may be used to form the whisk 220.

Referring to FIG. 2, cords 170 and hub 150 may form a whisk 220 that spins inside receptacle 105, with cords 170 sweeping along wall 110 and bowl 115. Cords 170 may be made of a flexible, resilient plastic or an elastic, synthetic polymer such as nylon, that exerts an upward force on hub 150 and a downward force on bowl 115, bowing at the sides and along wall 110 such that the when hub 105 rotates, cords 170 sweep across the entire inner surface of wall 110 and bowl 115 of receptacle 105. Cords may be made of nylon trimmer line, such as 0.080 diameter round trimmer line.

The materials used for mixing vessel 100, including receptacle 105, cords 170, lid 120, hub 150 and/or retainer ring 130 may be inexpensive nylon or plastic polymers, including polypropylene, acrylonitrile butadiene styrene (ABS), LDPE, high-density polyethylene (HDPE), and/or EVA. The total volume of plastic necessary for each mixing vessel 100 may be comparable to the amount of plastic in a cup of yogurt.

Mixing Machine

Figure 3:
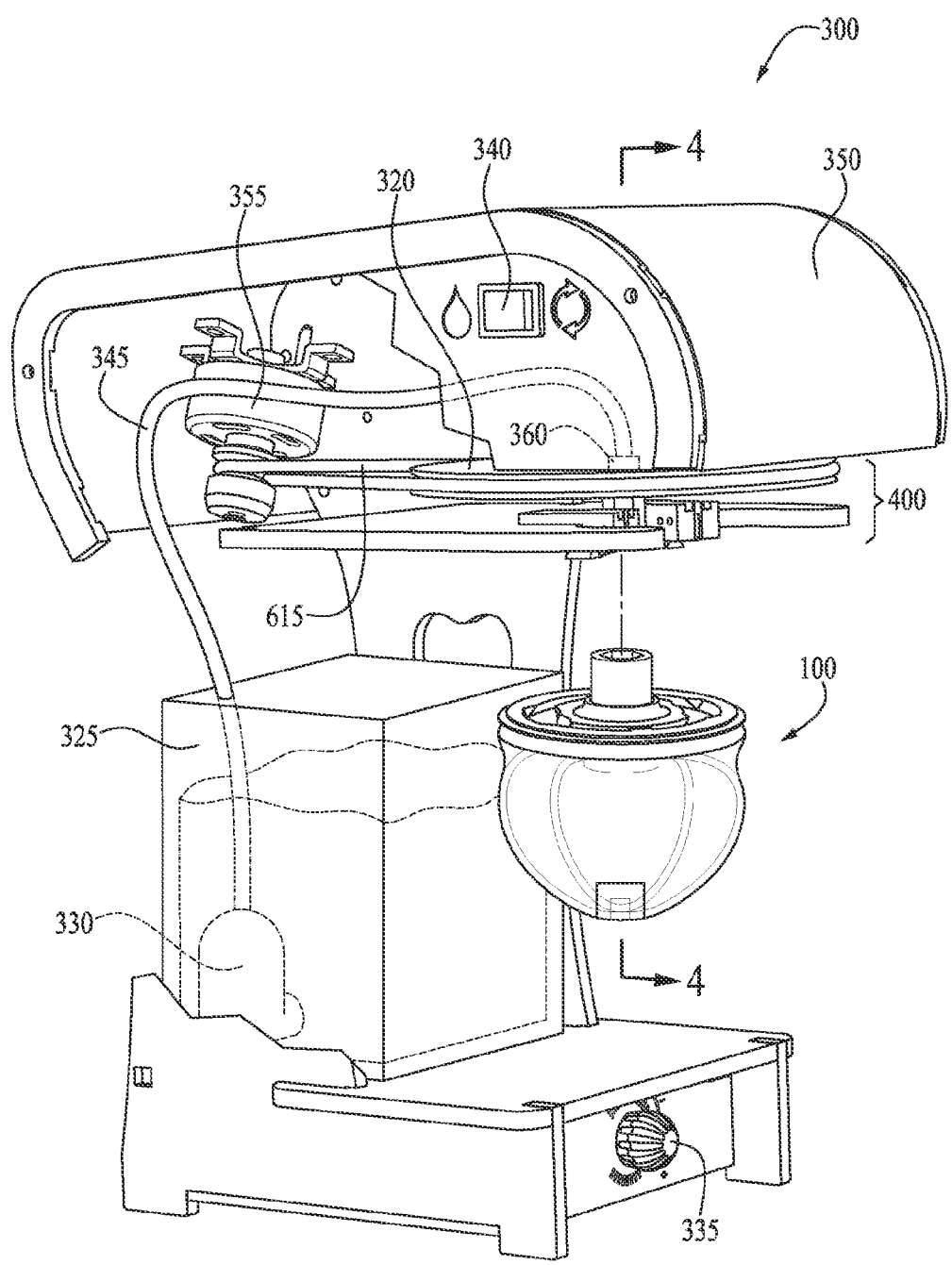
FIG. 3 is a perspective view, with part broken away, of a mixing machine of an illustrative embodiment.

A mixing machine may be used to dispense water into mixing vessel 100 and rotate whisk 220. FIG. 3 is an illustrative embodiment of a mixing machine. In some embodiments, mixing machine 300 may be lightweight, such as between about 1 and 5 pounds, and be about 11 inches in height and 10 inches in width and/or about the size of a small blender or coffee maker. Mixing machine 300 may operate off of alternative current or direct current. In the case of alternating current, mixing machine 300 may include a cord (not shown) to plug into a wall outlet. In the case of direct current, mixing machine 300 may be configured to operate off of batteries.

Figure 5:
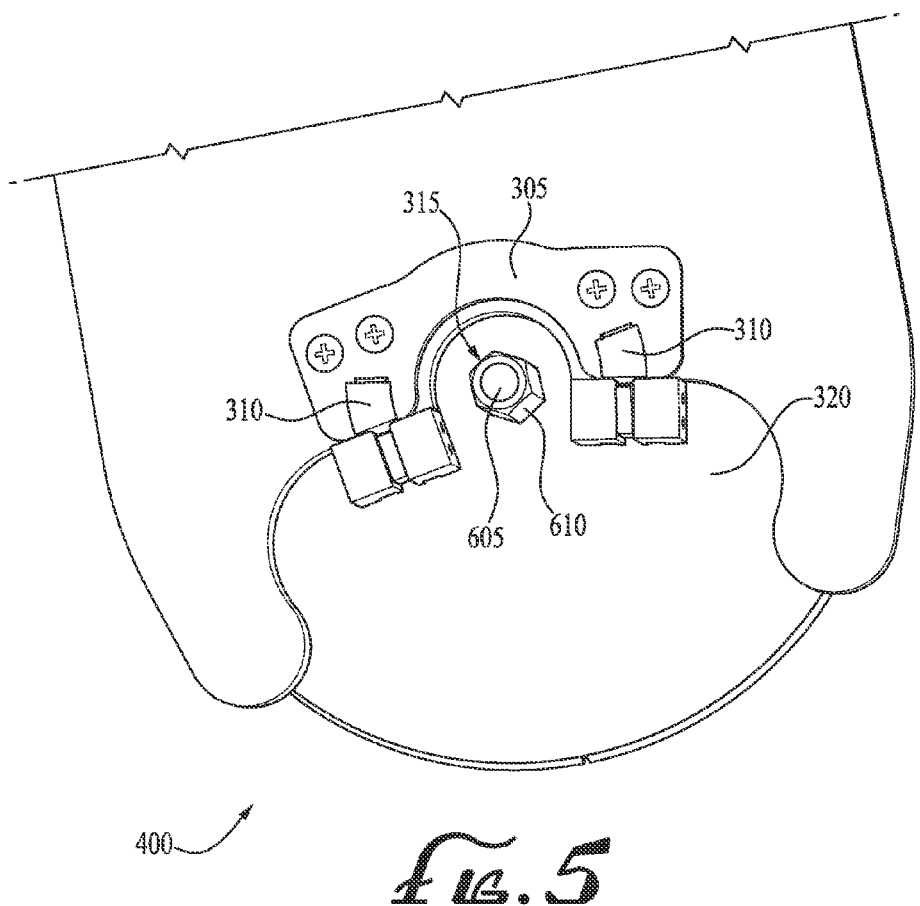
FIG. 5 is a plan view from below of a mixing axle of an illustrative embodiment.

Mixing machine 300 may include a mixing vessel 100 receiving and/or attachment area. An exemplary mixing vessel 100 receiving area 400 of mixing machine 300 is illustrated in FIG. 5. As shown in FIG. 5, mixing vessel 100 receiving area 400 includes a platform 305 with protuberances 310. Protuberances 310 may slide into depressions 145 on lid 120 to removeably lock mixing vessel 100 onto mixing machine 300. For example, a protuberance 310 may slide into a larger area of depression 145, and then as mixing vessel 100 is rotated lock into a narrower area of depression 145 to be held securely in place. To remove mixing vessel 100 from platform 305, an operator may rotate mixing vessel 100 in the opposite direction in order to slide protuberances 310 from the narrower area of depression 145 and into the wider area where protuberances 310 may fall out of depression 145. It may be appreciated that in other embodiments, lid 120 may include protuberances and platform 305 may include depressions. In yet other embodiments, mixing vessel 100 may clip, snap, stick or otherwise attach into place, such that it is attached to mixing machine 300 during water dispensing and mixing operations, but removable upon completion of the water dispensing and mixing operations.

Platform 305 may be in proximity to mixing axle 315, which may be hollow. Outer circumference of mixing axle 315 may form hub connector 610 and inner circumference of mixing axle 315 may form water conduit 605. Platform 305 may surround, partially surround and/or be situated adjacent to mixing axle 315. Mixing axle 315 may be hollow in order to dispense water into mixing vessel 100 through water conduit 605, as shown in FIG. 4. The outer circumference of mixing axle 315 may form hub connector 610 and be shaped to fit inside of, engage and/or mate with orifice 210 of hub 150. In FIGS. 2 and 5, hub connector 610 and orifice 210 are both shown hexagonal in shape, although other polygon or rounded, or lock and key configurations are possible. As shown in FIG. 4, when hub 150 is connected to hub connector 610 of mixing axle 315, water stream 410 may be dispensed through water conduit 605 and/or the hollow portion of mixing axle 315, through orifice 210 of hub 150, and into mixing vessel 100. Also when hub 150 is connected to hub connector 610 and lid 120 is attached to platform 305, whisk 220 including hub 150 and cords 170 may rotate with mixing axle 315, whilst lid 120 and receptacle 105 remain stationary. In some embodiments, hub connector 610 of mixing axle 315 may be brass. The shape of mixing axle 315 and its hollow interior assist in keeping dispensed water away from electrical components in the system of illustrative embodiments.

As shown in FIG. 4, mixing axle 315 may extend centrally and longitudinally through pulley 320, such that mixing axle 315 is parallel to the axis of rotation of pulley 320 and pulley 320 extends radially about mixing axle 315. Mixing axle 315 may be secured to pulley 320 and rotatable by pulley 320 using belt 615 (shown in FIG. 3), which belt 615 may be turned by motor 355.

Illustrative embodiments may provide for a predictable, leak-proof method of water delivery into mixing vessel 100. FIG. 4 illustrates an exemplary mixing vessel 100 attached to mixing machine 300 such that water stream 410 may be dispensed into mixing vessel 100 by mixing machine 300, and mixing machine 300 may mix the water with dental impression material 415 inside mixing vessel 100. When mixing vessel 100 is inserted onto the mounts (protuberances 310), hub 150 may mate with hub connector 610 of mixing axle 315. The hub 150 of the mixing vessel 100 may slide about hub connector 610 of mixing axle 315 like a sleeve and engage it at such an orientation that when mixing axle 315 turns, hub 150 also may rotate. Upward pressure imposed by cords 170 onto hub 150 may assist in securing the connection between mixing axle 315 and hub 150. With this pressure, hub 150 may be pushed onto the mixing axle 315 and held securely in place, which may prevent hub 150 from sliding off of mixing axle 315. In such embodiments, pumping force from water pump 330 or a faucet and gravity may contribute to a secure water delivery scenario as water flows through hollow mixing axle 315 and/or water conduit 605 of mixing axle 315. In some embodiments, hub 150 may be keyed to mixing axle 315 at a keyway (not shown). Mixing vessel 100 may receive water without leaking or spillage. The water may pass through the hollow mixing axle and/or water conduit 605 and into the mixing vessel 100 interior without coming back out. The flow, volume and pressure of water, sealing mechanism of lid 120 and retainer ring 130, and/or upward pressure of the cords 170 against the hub 150 all may contribute to creating barriers to leakage.

Returning to FIG. 3, water may be dispensed by mixing machine 300 from water receptacle 325, through flexible tubing 345, and then through water conduit 605 of mixing axle 315. Water receptacle 325 may be removable from mixing machine 300 so as to be easily filled with water from a tap or hose. A small submersible water pump 330, such as a micro submersible pump driven by a brushless motor may be used to pump water from water receptacle 325 to mixing vessel 100. In some embodiments, tubing 345 may attach to a water hose, faucet or nozzle and water receptacle 325 and/or water pump 330 may not be necessary. Dial 335 on mixing machine 300 may allow an operator to control the quantity of water that is dispensed into mixing vessel 100. For example, if an operator desired to mix dental alginate for an adult mouth, he or she may select 45 mL of water to be dispensed into mixing vessel 100. For thicker or thinner paste, another type of powder such as dental stone, or a child's mouth for example, another quantity of water may be selected.

In order to dispense the correct amount of water during each usage, a valve 360 may be employed in conjunction with water pump 330. Valve 360 may be placed at the entrance of water conduit 605 and may work synchronously with water pump 330. The water pump 330 and valve 360 may be controlled by a circuit board (not shown) with a programmed and/or inputted time interval. When the program is activated, for example by a push of switch 340 by the operator, the water pump 330 pushes water through tubing 345 while the valve 360 at the entrance to water conduit 605 and/or mixing axle 315 stays open. When the interval ends, the valve 360 may close and pump 330 may cease operations, and the water stops flowing. This cohesive operation of the pump 330 and valve 360 may allow for predictable water flow forward and a minimum of "suckback" (i.e., the water stays put in tubing 345 when valve 360 closes). The next water cycle then may start at the same point as the previous cycle and thus deliver substantially the same amount of water each time and/or deliver the amount of water selected by the operator, as entered with dial 335. Valve 360 may be a solenoid operated valve, a mechanical valve operated by a linkage or may be vacuum actuated.

A motor 355 may reside inside case 350 to cause rotation of mixing axle 315. Motor 355 may be a brushless motor, an electronically commutated motor, an induction motor, a permanent magnet synchronous motor and/or another type of motor capable of causing rotation in both a clockwise and counter-clockwise direction. Rotation in two directions may assist in complete, thorough mixing of the dry impression material 415 and water 410. In instances where whisk 220 turns only in a single direction pooling of the material may occur inside mixing vessel 100. Mixing bi-directionally may assist in combating pooling of material. In certain embodiments, mixing in only a single direction may be necessary.

Motor 355 may operate to turn pulley 320 using belt 615. Belt 615 may be wrapped about both pulley 320 and motor 355 such that the rotation of motor 355 is conveyed to pulley 320. Mixing axle 315 may be fixedly secured to pulley 320, extending longitudinally through pulley 320 and parallel to pulley 320's axis of rotation.

In some embodiments, a 730 kv rpm motor, with a 5.0 mm shaft, 11.1-14.8 volts and no-load current of 1.9 amps at 11.1 volts and 330 maximum wattage may be employed as motor 355. A lower voltage motor may reduce the possibility of electrical shock to the operator. In presently preferred embodiments, motor 355 should operate off DC current, be compact, deliver sufficient torque, deliver an acceptable range of RPM's (such as 200-500), be programmed to turn, stop and then turn in the opposite direction, be readily available and be relatively inexpensive. A HobbyKing Donkey ST3508-730 kv brushless motor or similar is a suitable motor.

Directing the water away from the motor also may assist in preventing against electrical shock. Case 350 may be at the top of mixing machine 300 as illustrated in FIG. 3, or alternatively may be placed at the base of mixing machine 300. In instances where case 350 is at the top of mixing machine 300, motor 355 may be placed about 6-8 inches behind mixing axle 315 where water flows. A bridge rectifier may be employed such that motor 355 may run off of either AC or DC power as required. In certain embodiments, motor 355 may be pre-programmed to operate in a rotation cycle whereby it automatically alternates rotation directions once turned on in mixing mode.

Switch 340 may allow an operator to turn mixing machine 300 on or off, or switch from a water dispensing to a mixing function. Switch 340 may also allow an operator to select whether the motor rotates in a clockwise or counter-clockwise direction. In certain embodiments, motor 355 may be pre-programmed to operate in a rotation cycle whereby it automatically alternates the direction of rotation.

Operation of the Mixing Machine

Figure 7:
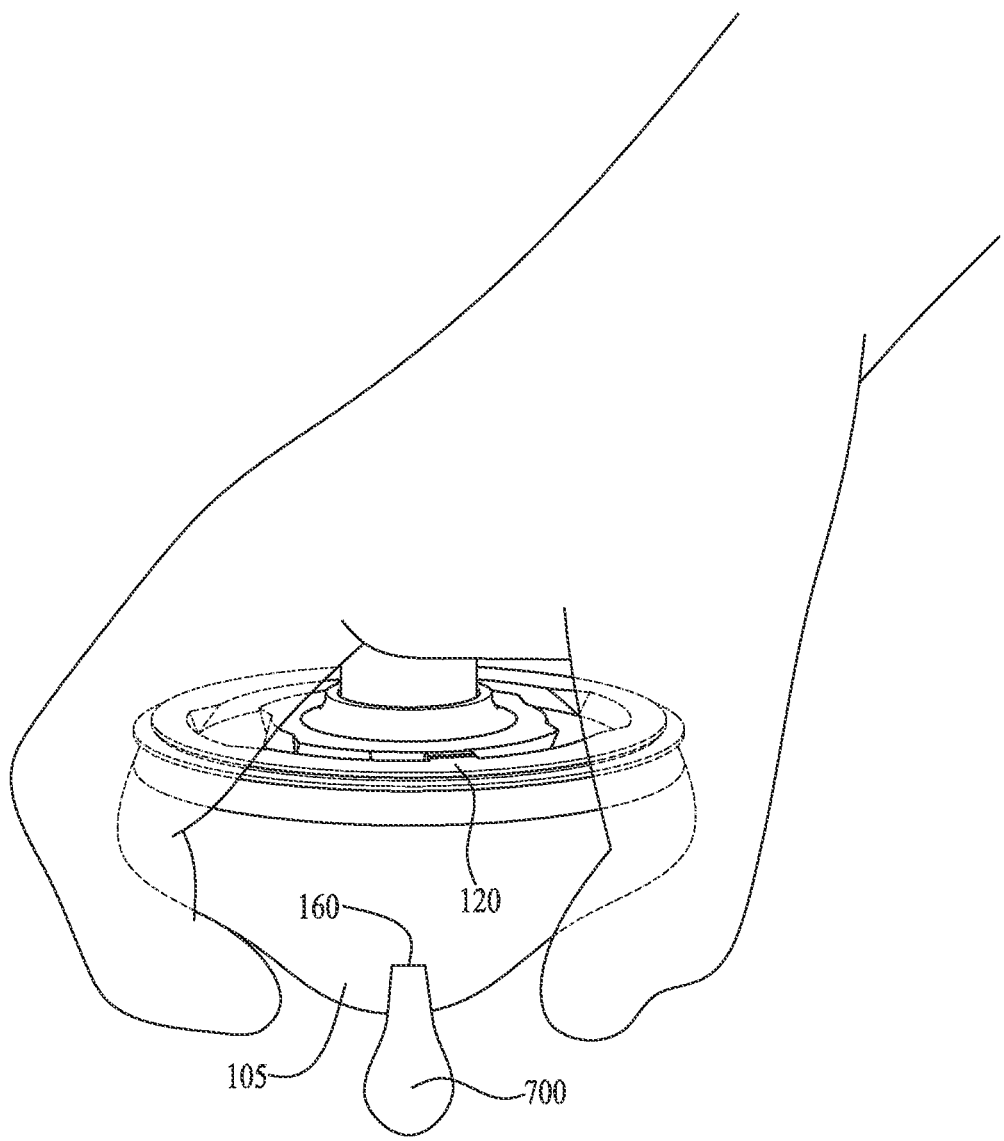
FIG. 7 is a perspective view of a mixing vessel of an illustrative embodiment during dispensation of mixed paste.

Once mixing vessel 100 is mounted on platform 305, mixing machine 300 may be activated by pressing, touching or otherwise activating switch 340. Switch 340 may start a preset water delivery cycle followed by a mixing cycle that is determined by the operator. All dispensing of water and mixing is done by mixing machine 300. The operator simply presses switch 340 to accomplish all of the steps to obtain thoroughly mixed dental impression material. Once the cycle is stopped, the mixing vessel may be untwisted, slid or otherwise removed from protuberances 310. The operator then holds mixing vessel 100 in one hand and removes adhesive 160 with the other hand. The paste may then be squeezed out with the gripping hand like paste out of a tube. FIG. 7 illustrates an exemplary mixing vessel 100 as it is being collapsed to dispense mixed paste 700. As shown in FIG. 7, receptacle 105 may collapse when squeezed, but lid 120 may not. In some embodiments, dispensing of mixed paste 700 is accomplished by the operator's palm forcing down the lid 120 to the base of the bowl 115 in a fashion similar to the action of squeezing a tennis ball.

Figure 6:
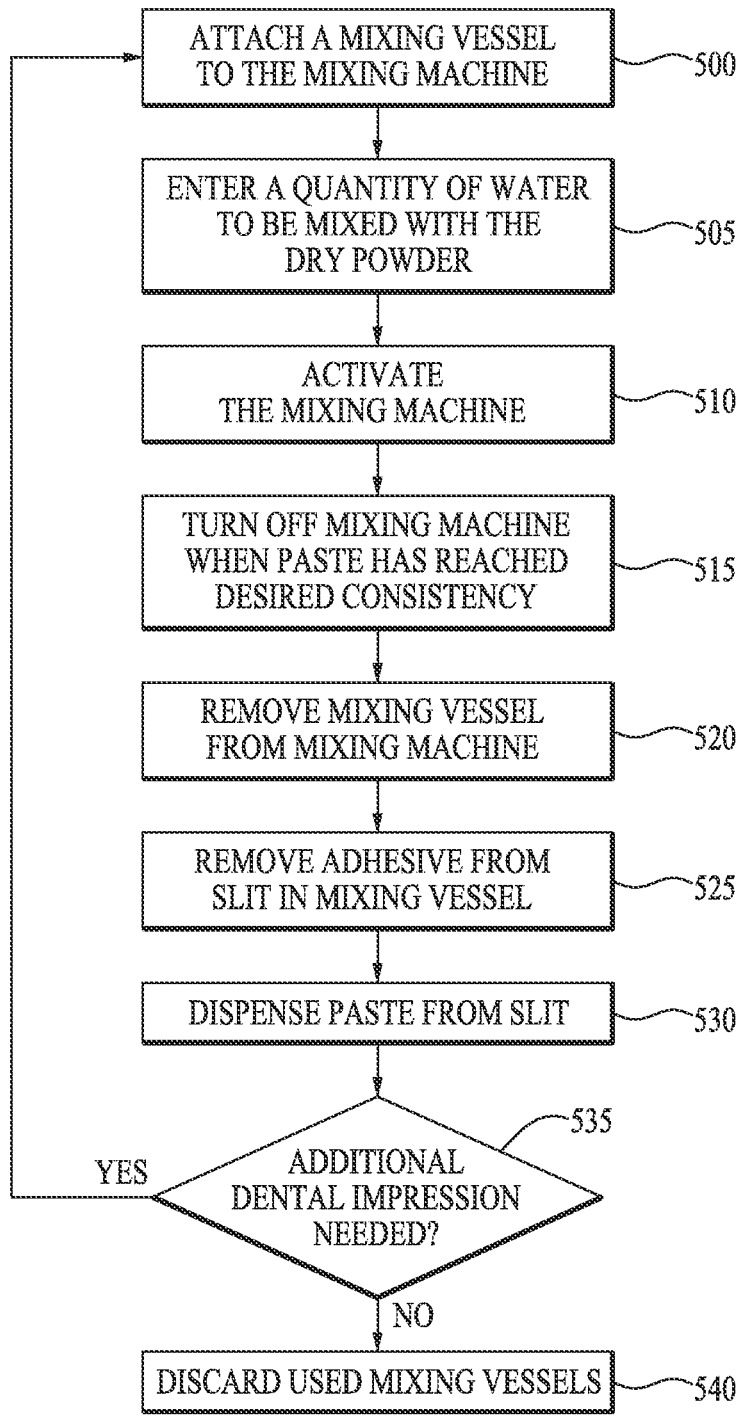
FIG. 6 is a flowchart of a method of mixing and dispensing dental impression material of an illustrative embodiment.

This process may be repeated a first time for dental alginate to create the paste that will form the dental impression, and then a second time for the dental stone to create the paste that will form the dental cast. A separate, disposable mixing vessel 100 that contains the correct amount and type of dry powder may be used for each step. An exemplary method for mixing and dispensing dental impression material is illustrated in FIG. 6. A user may first attach a disposable mixing vessel 100 to mixing machine 300, the disposable mixing vessel 100 comprising a specific, pre-measured amount of dry alginate powder at step 500. For example, the user may attach protuberances 310 to depressions 145 by lightly pressing and twisting mixing vessel 100 into place on platform 305. At step 505, the user may then enter into mixing machine 300 a quantity of water to be mixed with the dry alginate powder by mixing machine 300, for example by turning dial 335. The user then activates the mixing machine 300 to dispense the quantity of water and mix the quantity of water with the dry powder to form a paste, for example by pressing switch 340 at step 510. Once switch 340 has been pressed, mixing machine 300 may proceed through a pre-programmed mixing cycle that may alternate direction of rotation. When the machine has reached the desired consistency, the user may turn switch 340 off at step 515. A transparent receptacle 105 may assist in allowing the user to view when the paste has reached the correct consistency. Alternatively, the mixing machine 300 may be programmed to stop based upon pre-programmed timing and step 515 may not be necessary. The user may then remove mixing vessel 100 from the mixing machine at step 520 and remove adhesive 140 from slit 160 in the disposable mixing vessel 100 at step 525. The user may then squeeze the disposable mixing vessel 100 to dispense the paste from the slit 160 in the disposable mixing vessel 100 and into a dental tray at step 530. This process may be repeated at step 535 if additional paste is needed for the cast. Used mixing vessels 100 may be discarded at step 540. Used mixing vessel(s) 100 may be discarded at any point after the mixed paste has been dispensed from them.

Illustrative embodiments may provide consistent mixing and dispensing of dental impression material in a fashion that reduces the labor intensiveness of the process as compared to conventional systems and methods. Using illustrative embodiments, the need for a technician to measure and/or handle dry powder may be eliminated. Thorough mixing of water with dry powder may be accomplished in an expedient manner with a predictable force and paste consistency, and a reduced risk of bubbles, clumping or slumping. Mixed impression paste may be blended and dispensed in a cost-efficient disposable mixing vessel that may eliminate the need to clean and/or sterilize mixing cups and utensils and therefore reduce the manpower otherwise needed to do so.

Thus, the invention described here provides one or more embodiments of an apparatus, system and method for mixing and dispensing dental impression materials. While the invention herein disclosed has been described by means of specific embodiments and applications thereof, numerous modifications and variations could be made thereto by those skilled in the art without departing from the scope of the invention set forth in the claims. The foregoing description is therefore considered in all respects to be illustrative and not restrictive. The scope of the invention is indicated by the appended claims, and all changes that come within the meaning and range of equivalents thereof are intended to be embraced therein.

What is claimed is:

1. A dental impression material mixing system comprising:
    a mixing vessel comprising:
        a rounded bowl forming a bottom of the mixing vessel, the rounded bowl having a slit at a base and comprising a removable adhesive sealedly enclosing the slit; and
        a flexible wall contiguous with the rounded bowl;
    a lid secured on the flexible wall;
    a tubular rotatable hub having apertures, the tubular rotatable hub fit into the lid;
    a flexible cord threaded through the apertures of the tubular rotatable hub to form at least two loops of the flexible cord, the at least two loops extending from the tubular rotatable hub contouredly along an inner surface of the flexible wall and rounded bowl, wherein the at least two loops cross each other at the base; and
    a mixing machine, the mixing machine comprising a rotatable hub connector and a water conduit;
    the tubular rotatable hub removeabley coupled to the rotatable hub connector; and
    wherein the mixing machine is configured to dispense water through the water conduit into the mixing vessel and further configured to rotate the at least two loops of flexible cord such that dry dental impression material is hydrated and mixed to form a dental impression paste.

2. The dental impression material mixing system of claim 1, further comprising a platform surrounding the hub connector, wherein the platform is mateable with a lid of the mixing vessel.

3. The dental impression material mixing system of claim 1, wherein a premeasured amount of the dry dental impression material is sealed within the mixing vessel.

* * * * *